United States Patent
Amarasinghe et al.

(10) Patent No.: US 8,413,657 B2
(45) Date of Patent: *Apr. 9, 2013

(54) MASK BRACE AND MASK ASSEMBLY

(75) Inventors: Amal Shirley Amarasinghe, West Pennant Hills (AU); Robert Henry Frater, Lindfield (AU)

(73) Assignee: ResMed Limited, Bella Vista (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/271,669

(22) Filed: Oct. 12, 2011

(65) Prior Publication Data

US 2012/0024291 A1 Feb. 2, 2012

Related U.S. Application Data (63) Continuation of application No. 10/433,564, filed as application No. PCT/AU01/01578 on Dec. 7, 2001, now Pat. No. 8,042,541.

(30) Foreign Application Priority Data

Dec. 7, 2000 (AU) ........................................ PR1933

(51) Int. Cl.
*A62B 18/08* (2006.01)
*A62B 18/02* (2006.01)
*A62B 9/04* (2006.01)
*A62B 18/00* (2006.01)
*A62B 9/00* (2006.01)

(52) U.S. Cl. ......... 128/207.11; 128/206.27; 128/206.21; 128/205.25; 128/202.27; 128/200.24

(58) Field of Classification Search ............. 128/202.27, 128/203.29, 205.25, 206.12, 206.16, 206.17, 128/206.24, 206.27, 207.11

See application file for complete search history.

(56) References Cited

U.S. PATENT DOCUMENTS

| 580,511 | A | 4/1897 | Scheerer |
| 787,828 | A | 4/1905 | Clayton |
| 2,011,733 | A | 8/1935 | Shindel |
| 2,079,581 | A | 5/1937 | Whipple |
| 2,444,417 | A | 7/1948 | Bierman |
| 2,875,757 | A | 3/1959 | Galleher, Jr. |
| 3,599,635 | A | 8/1971 | Ansite |
| 3,977,432 | A | 8/1976 | Vidal |

(Continued)

FOREIGN PATENT DOCUMENTS

| DE | 3927038 | 2/1993 |
| DE | 10035946 | 6/2000 |

(Continued)

OTHER PUBLICATIONS

Final Notice of Reasons for Rejection mailed Jan. 17, 2012 in Japanese Appln. No. 2009-137364, with English Translation (3 pages).

(Continued)

*Primary Examiner* — Annette Dixon
(74) *Attorney, Agent, or Firm* — Nixon & Vanderhye P.C.

(57) ABSTRACT

A patient mask assembly for positive pressure ventilation includes a brace which clips to the mask and provides attachment locations for headgear straps in alternative positions to those attachment locations which may be provided by the mask. The brace may also provide a mask stabilizing portion.

22 Claims, 5 Drawing Sheets

U.S. PATENT DOCUMENTS

| | | | |
|---|---|---|---|
| 4,231,363 | A | 11/1980 | Grimes |
| 4,630,604 | A | 12/1986 | Montesi |
| 4,944,310 | A | 7/1990 | Sullivan |
| 4,951,664 | A | 8/1990 | Niemeyer |
| 5,005,571 | A | 4/1991 | Dietz |
| 5,243,971 | A | 9/1993 | Sullivan et al. |
| 5,245,995 | A | 9/1993 | Sullivan et al. |
| 5,560,354 | A | 10/1996 | Berthon-Jones et al. |
| 5,617,849 | A | 4/1997 | Springett et al. |
| 5,647,357 | A | 7/1997 | Barnett et al. |
| 5,662,101 | A | 9/1997 | Ogden et al. |
| 5,687,715 | A | 11/1997 | Landis et al. |
| 5,921,239 | A | 7/1999 | McCall et al. |
| 5,953,848 | A | 9/1999 | Darnell et al. |
| 6,019,101 | A | 2/2000 | Cotner et al. |
| 6,119,693 | A | 9/2000 | Kwok et al. |
| 6,123,082 | A | 9/2000 | Berthon-Jones et al. |
| 6,192,886 | B1 | 2/2001 | Rudolph |
| 6,422,238 | B1 | 7/2002 | Lithgow |
| 6,491,034 | B1 | 12/2002 | Gunaratnam et al. |
| 6,513,526 | B2 | 2/2003 | Kwok et al. |
| 6,631,718 | B1 | 10/2003 | Lovell |
| 6,712,072 | B1 | 3/2004 | Lang |
| 6,789,543 | B2 | 9/2004 | Cannon |
| 8,042,541 | B2 * | 10/2011 | Amarasinghe et al. .. 128/207.11 |
| 2004/0025882 | A1 | 2/2004 | Madaus et al. |
| 2006/0174892 | A1 | 8/2006 | Leksutin et al. |
| 2007/0062537 | A1 | 3/2007 | Chiesa et al. |
| 2007/0101997 | A1 | 5/2007 | Chiesa et al. |

FOREIGN PATENT DOCUMENTS

| | | |
|---|---|---|
| EP | 1 892 006 A1 | 2/2008 |
| FR | 2720280 | 12/1995 |
| GB | 2176404 A | 12/1986 |
| JP | 51-29793 | 8/1976 |
| JP | 3039303 U | 4/1997 |
| JP | 2001-511035 A | 8/2001 |
| JP | 2002-526180 A | 8/2002 |
| WO | WO 98/12965 | 4/1998 |
| WO | WO 99/61088 | 12/1999 |
| WO | WO 2006/074273 A2 | 7/2006 |

OTHER PUBLICATIONS

Supplementary Partial European Search Report mailed Jul. 2, 2007 in European Application No. 01999401.1.

* cited by examiner

MASK BRACE AND MASK ASSEMBLY

CROSS-REFERENCE TO RELATED APPLICATIONS

This application is a continuation of Ser. No. 10/433,564, filed Jun. 5, 2003, which is the U.S. national phase of International Application No. PCT/AU01/01578, filed Dec. 7, 2001, which designated the U.S. and claims priority to Australian Application No. PR 1933, filed Dec. 7, 2000, the entire contents of each of which are hereby incorporated by reference.

BACKGROUND OF THE INVENTION

1. Field of the Invention

The invention relates to the configuration, fitting and operation of a mask suitable for the delivery of non-invasive positive pressure ventilation and for nasal CPAP treatment of sleep disordered breathing conditions such as obstructive sleep apnea.

2. Description of Related Art

Obstructive Sleep Apnea (OSA) is a disease characterized by excessive daytime sleepiness, loud snoring and daytime irritability. Other effects of OSA can include depression, high blood pressure, serious heart conditions, sexual problems, memory lapses, intellectual deterioration and morning headaches. The treatment of OSA by the application of nasal Continuous Positive Air Pressure (CPAP) was invented by Sullivan and is described in U.S. Pat. No. 4,944,310 (Sullivan, assignee ResMed Limited). The technique involves the application of a flow of pressurized breathable gas (typically room air) to either the nose or nose and mouth of a patient while they sleep. This technique is said to "splint" open the airways. Typical treatment pressures are in the range of 3 to 20 cm $H_2O$. Flows are up to approximately 200 L/min. Usually the flow of pressurized air is produced by a blower and delivered to the patient via a patient interface. The source of the air flow and patient interface are joined by a conduit. Whilst there are other techniques for the treatment of OSA such as surgery, the use of CPAP has become the "gold" standard. For a particular patient the pressure which is needed to maintain open airways can vary throughout the night and vary on different nights. U.S. Pat. No. 5,245,995 (Sullivan and Lynch, assignee ResMed Limited) describes a method and device for varying the pressure in accordance with indications. For example, if the patient starts to snore, the pressure automatically increases, whilst in the absence of snoring the pressure automatically decreases.

Non-Invasive Positive Pressure Ventilation (NIPPV) is another form of treatment for breathing disorders. In its most basic form it involves a relatively higher pressure of gas being provided in the patient mask during the inspiratory phase of respiration and a relatively lower pressure or atmospheric pressure being provided in the patient mask during the expiratory phase of respiration. Typical treatment pressures are in the range of 3 to 30 cm $H_2O$.

In other NIPPV modes the pressure can be made to vary in a complex manner throughout the respiratory cycle. For example, the pressure at the mask during inspiration or expiration can be varied through the period of treatment, as disclosed in international PCT patent applications PCT/AU97/00631 (Berthon-Jones, assignee ResMed Limited) and PCT/AU99/00386 (Berthon-Jones, assignee ResMed Limited).

In this specification, any reference to CPAP treatment is to be understood as embracing all of the above-described forms of ventilatory treatment or assistance.

One of the earliest patient interfaces for providing CPAP treatment was constructed to include a fiberglass model of the patient's nose. The model was adhered to the patient's nose each night and removed each morning An advantage of this patient interface included the customized fit which assisted in achieving a good seal between the patient interface and the patient's airways. However the use of adhesive to secure the mask was inconvenient and not desirable.

Another suitable patient interface is described in U.S. Pat. No. 5,243,971 (Sullivan and Bruderer, assignee University of Sydney) entitled "Nasal Mask for CPAP having Ballooning/Moulding Seal with Wearer's Nose and Facial Contours".

This patent describes a nasal mask with a soft face-contacting portion and a rigid shell. The mask is held in position using headgear. The headgear is attached to the mask shell and passes around the back of the wearer's head. The patent depicts two sets of straps in the headgear. The first set comprised a pair of straps passing from the forehead region to the back of the head. The second set comprised a pair of straps passing from the nasal region of the mask to the back of the head.

Another known patient interface is the MIRAGE® nasal mask (by ResMed Limited). This nasal mask includes a pair of headgear attachment points in the nasal region of the mask shell and a forehead support which includes another pair of headgear attachment points. The forehead support to this mask is the subject of U.S. Pat. No. 6,119,693 (Kwok, Matchett & Grant, assignee ResMed Limited). The headgear comprises a single piece of a soft, flexible composite fabric with a generally triangular back portion and four straps. The four straps comprise a pair of upper straps and a pair of lower straps connecting to the headgear attachment points on the forehead support and nasal mask shell respectively. At the end of each strap is secured a piece of hook and loop fastening material such as Velcro™ which, in use, passes through a headgear attachment point and fastens on corresponding loop material on the strap. The generally triangular back portion engages the skull in the region of the occiput. The fabric stretches under a load. The base of the triangle is positioned near and generally in line with the upper straps.

Some patients open their mouths during sleep which means that they may not receive the benefit of nasal CPAP due to mouth leaks. Various solutions have been proposed for this problem. One solution is taught in U.S. Pat. No. 6,123,082 (Berthon-Jones, assignee ResMed Limited), whereby the lips are held closed. Another solution is to use a mask which covers both the nose and mouth of the patient. An example of a mouth and nasal mask is described in U.S. Pat. No. 5,560,354 (Berthon-Jones, Calluaud, Lynch & Hely, assignee ResMed Limited).

Figure 1:
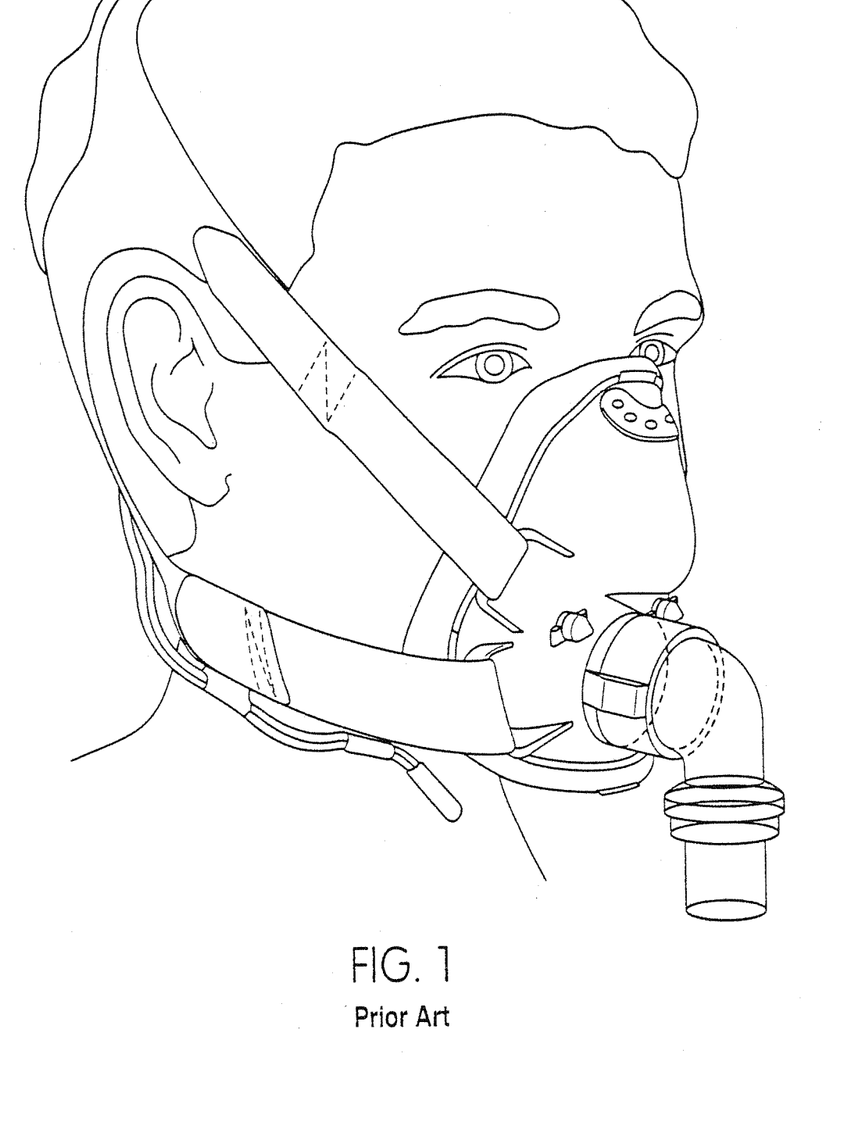
FIG. 1 shows a prior art full-face mask system located on a user's face.

Another suitable mask system is the MIRAGE® full face mask (by assignee ResMed Limited). The MIRAGE® full face mask and headgear is illustrated in FIG. 1. Suitable headgear for this mask is constructed from a composite material of nylon, neoprene and hook and loop material. The headgear similarly comprises a pair of upper and a pair of lower straps and a generally triangular back portion. The upper strap has a total length of approximately 610 mm. The straps have an approximate width of 25 mm, however the upper strap has an approximate width of 19 mm. The triangular region has a base of approximately 15.5 cm and two equal sides of approximately 11 cm. The upper and lower straps are approximately 192 mm apart. In addition, the headgear includes a quick release mechanism as described by U.S. Pat. No. 6,422,238 (Lithgow, assignee ResMed Limited). The quick release mechanism provides a "rip cord" which can be pulled upon to separate the headgear and hence remove the mask in an emergency. When the headgear is positioned on the patient's head, the quick-release mechanism is situated at the back of the head and the cord runs through loops towards the front of the mask system.

Patient interface arrangements include nasal masks, nose and mouth masks, nasal prongs and nasal pillows. In all forms of patient interface used with CPAP for treating sleep disordered breathing, there is a need to counterbalance the force of the pressurized air and to correctly position the interface. Since the patient must sleep with this interface, it is important that it be comfortable. From the manufacturing and distribution channel perspectives, it is advantageous if one size of headgear fits a large range of head shapes and sizes.

Other examples of prior art headgear and mask shells have configurations which are different to those depicted in U.S. Pat. No. 5,243,971 and used in the MIRAGE® nasal mask and MIRAGE® full-face mask in so far as they incorporate a different number of headgear straps or differ in the placement of the head strap attachment points or both. This variety of mask configurations is required to address the biological variability existing between users, each user having a unique facial and. head shape. However no one mask system involving headgear and fixed point strap attachment points offers continuous variability in placement. As a result, when selecting from a range of mass produced mask and headgear systems, in the majority of cases the selection will represent a compromise for the user where a balance must be struck between comfort and the achievement of a secure fit and good seal between the mask and the user.

An approach to headgear attachment which allows for great variability in head strap number and attachment position to the mask would yield great benefits to the user in terms of comfort and function, to the mask system manufacturer in terms of facilitating the opportunity to easily experiment with different mask positions and headgear configurations while moving towards the desirable objective of rationalising manufacturer and supplier inventory.

It should be noted that while there are many mask and headgear arrangements available for ventilators, respirators, aviator masks and other breathing apparatus, generally these may not be suitable for use in the treatment of sleep disordered breathing because they are not sufficiently comfortable to allow the patient to sleep.

The present invention is directed towards providing a method of configuring a mask and a mask for use in the treatment of sleep disordered breathing which improves patient comfort, is long lasting and fits a wide range of head shapes and sizes.

SUMMARY OF THE INVENTION

The present invention relates to an improvement to the method and apparatus for the positioning and attachment of headgear to a patient interface such as a mask.

The invention includes the incorporation of a brace into the mask which is independent of the mask shell, said brace being adapted in use to be held in a substantially fixed position relative to the mask shell and to accommodate the attachment of at least part of the headgear.

The present invention enables the attachment points for headgear to be determined and varied in a physical or temporal sense independently of the mask shell configuration.

The invention broadly resides in a brace for a patient airway interface, the brace being shaped so as to be retainingly engageable with the interface and providing at least one formation for engagement with a headgear member.

Preferably the brace includes an elongate member shaped so as to be engageable by formations on said interface.

The invention also broadly resides in a brace for a patient airway interface, the brace being shaped so as to be retainingly engageable with the interface, the brace further including a formation disposed for engagement with the patient's forehead.

DESCRIPTION OF PREFERRED EMBODIMENTS OF THE INVENTION

Figure 2:
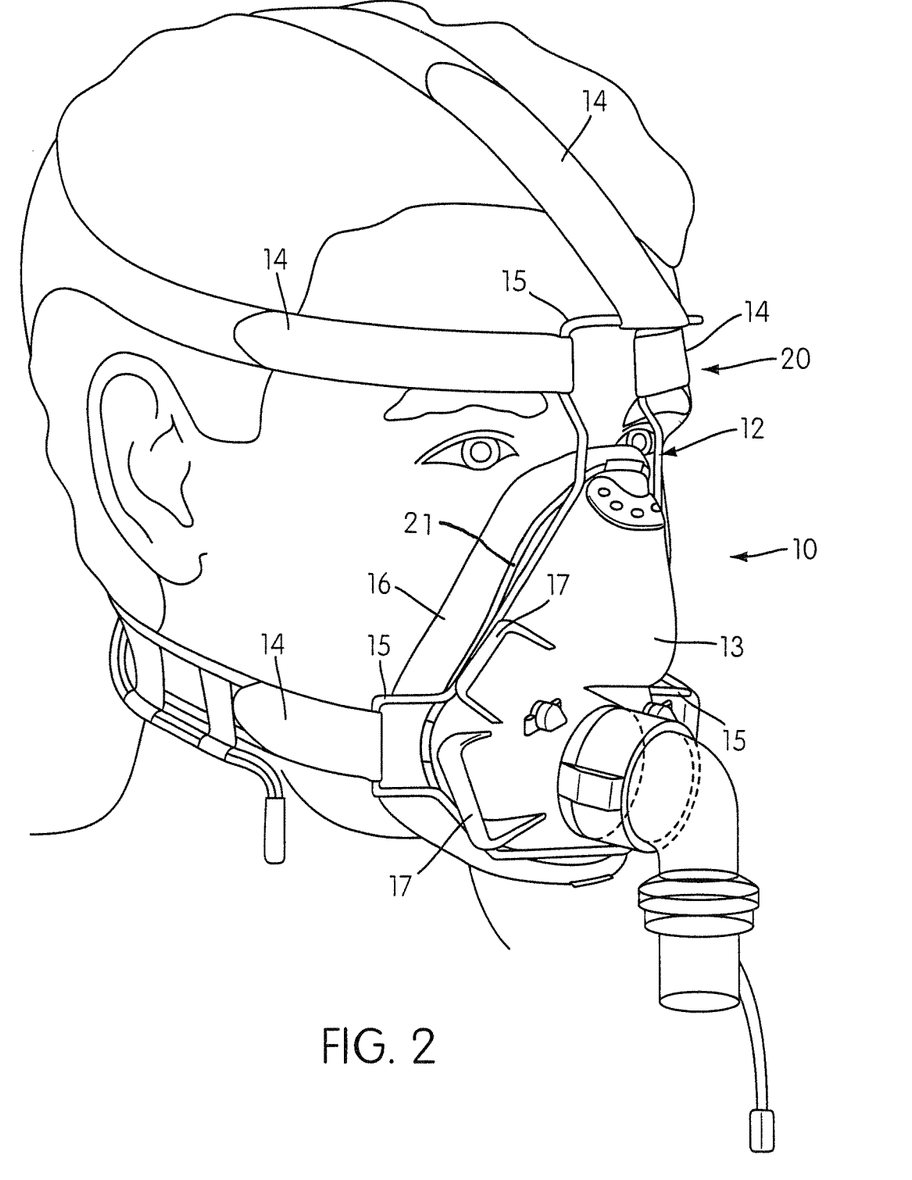
FIG. 2 shows a mask system incorporating a brace according to the present invention located on a user's face.

FIG. 2 shows a mask system 10 incorporating the present invention consisting of a brace 12, mask shell 13, headgear straps 14, brace head strap attachment points 15, mask cushion 16 and mask shell headgear attachment points 17.

It will be immediately apparent that the headgear attachment points 17 of the mask shell are superfluous in this embodiment of the present invention so far as concerns their original intended role as attachment points for the headgear. This is because the headgear attachment points of the brace serve the requisite purpose independently of any attachment point of the mask shell. Nevertheless because it is intended that the brace assume a fixed predetermined position with respect to the mask shell, existing mask shell headgear attachment points 17 can serve as retaining formations for the brace.

While the brace depicted in FIG. 2 has provision for attaching five headgear straps, the brace may be configured so as to receive any suitable number. The present invention envisages the brace assuming a substantially constant position relative to the mask shell when the mask assembly is properly located on the user. It may be configured to receive at least as many headgear straps as are required for a particular headgear configuration or alternatively may have less than or more headgear attachment points with respect to any particular headgear configuration.

The versatility of the present invention will be immediately apparent to those skilled in the art in that for any given mask shell, it is possible to configure a brace so as to receive the requisite number of headgear straps and to locate the brace headgear attachment points in such locations as to allow a user to choose between a variety of headgear configurations. This versatility allows the user to optimise their choice of headgear as the particular requirements may dictate so as to achieve the requisite mask seal and comfort.

A user may be supplied with a number of braces each with a different number of headgear attachment points or at least having a set number of headgear attachment points positioned in a variety of configurations with respect to the mask shell in order that a suitable choice may be made.

In an embodiment of the invention, the brace is designed so as to achieve a "clip fit" on an existing mask frame as previously described.

Figure 3:
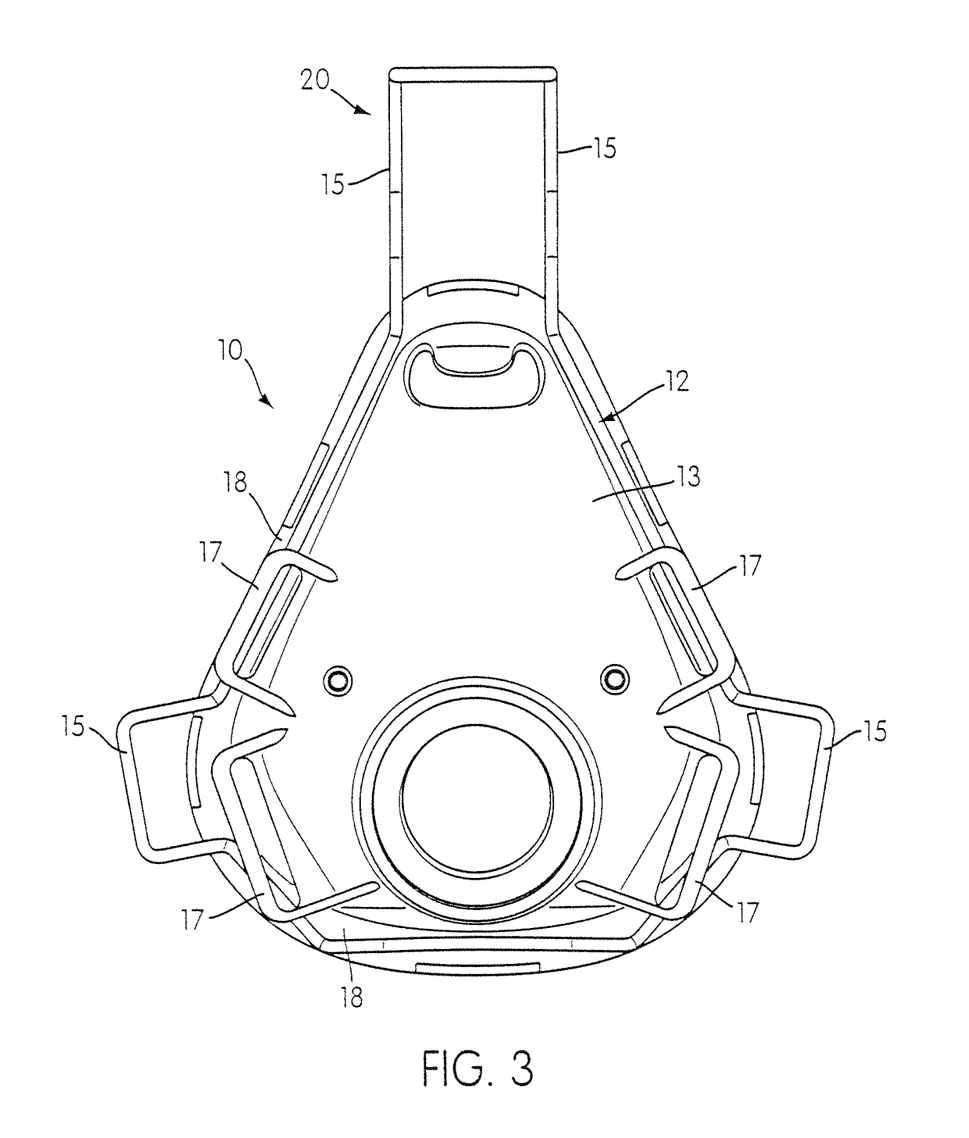
FIG. 3 shows a brace according to the present invention located on a mask shell.
Figure 4:
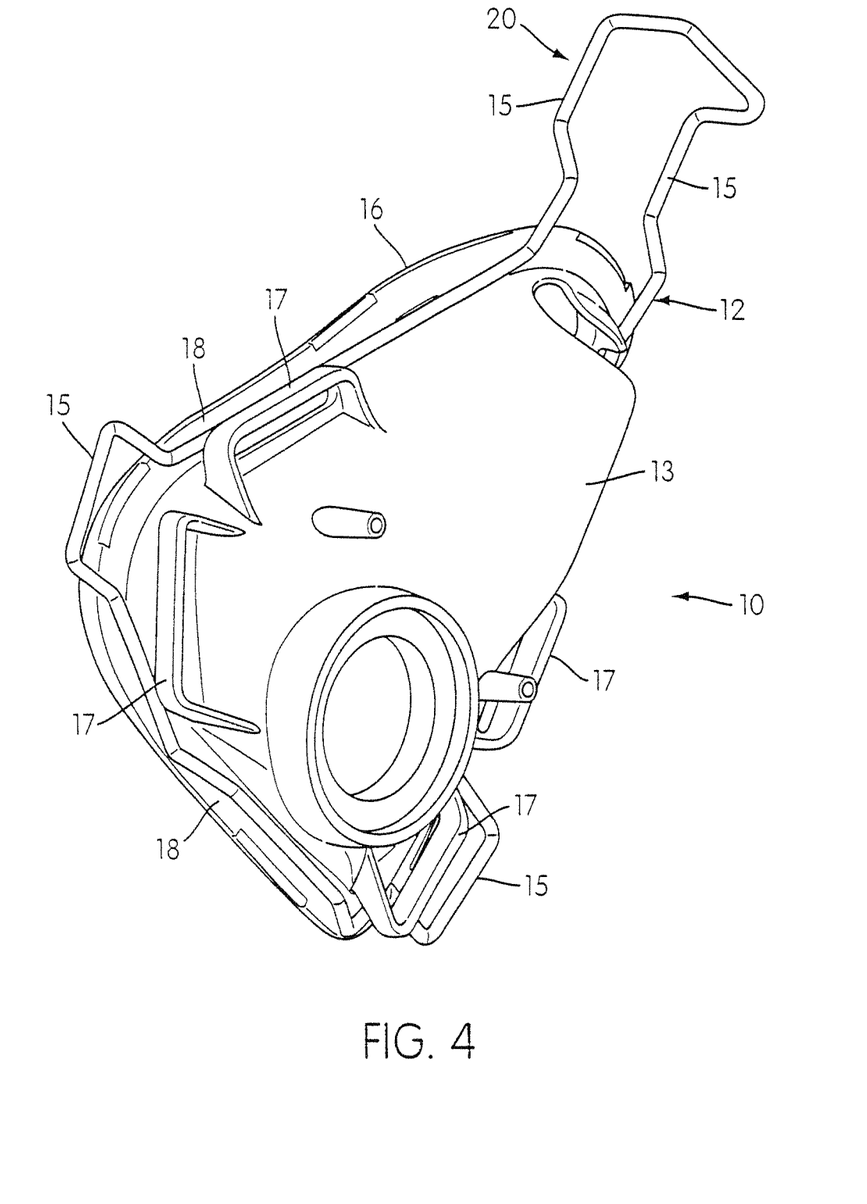
FIG. 4 shows another view of the brace and mask of FIG. 3, and FIGS. 5A-5D show different perspectives of a brace according to the present invention.
Figure 5A:
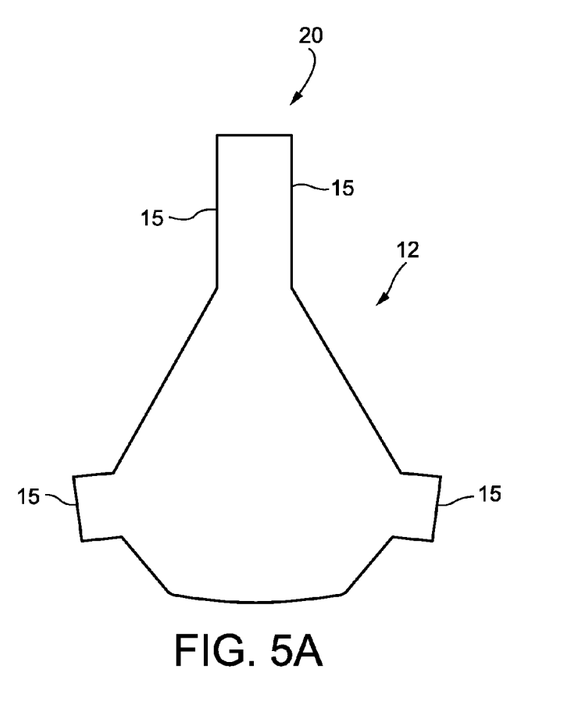
Figure 5B:
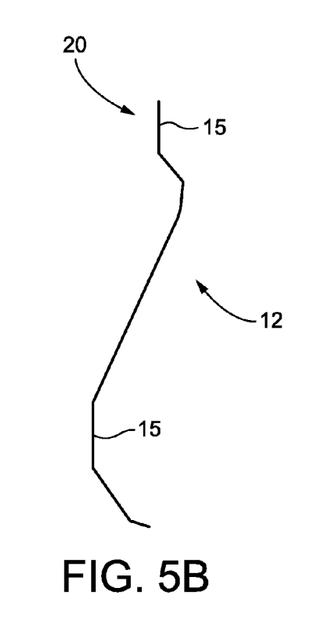
Figures 5C, 5D:
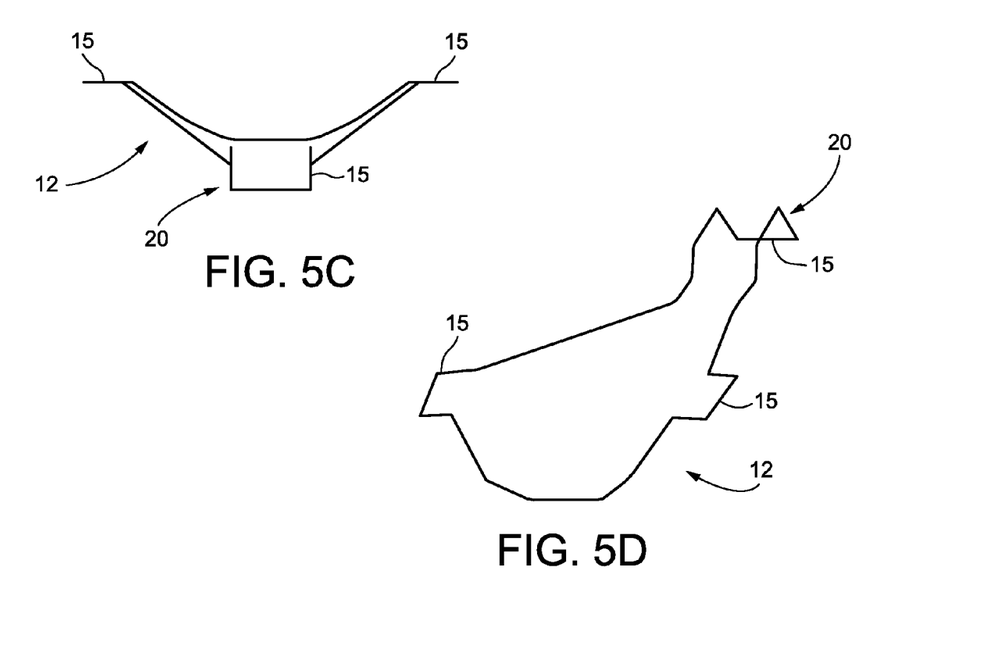

FIG. 3 illustrates a clip fit arrangement in which a brace 12 is fitted between the existing mask frame headgear attachment points 17 and the mask shell outer surface, in this case the peripheral flange portion 18. Where headgear strap attachment points 17 are provided for on the mask shell they may be used in conjunction with some or all of the headgear strap attachment points 15 of the brace 12 thereby providing further flexibility in the configuration.

In an alternative embodiment of the invention (not illustrated) suitable engagement points may be created within the mask shell so as to receive the brace, such attachment points being designed so as not to be suitable for attaching headgear straps.

Because of the versatility offered by the brace of the present invention, it also offers the possibility for incorporating a mask stabilising feature independent of or in addition to the inclusion of the headgear attachment points. An example of such a stabilizing feature is illustrated in the accompanying drawings in the form of a forehead stabilising section 20. The stabilizing portion 20 takes the form of a portion of the brace extending clear of the mask shell so as to provide an elevated engagement point and/or to contact a portion of the user's face, in this case the forehead. The malleability of the wire used to form the brace allows the position of the stabilizing portion to be adjusted for individual patients. In FIG. 2 it can be seen that the forehead stabilising portion 20 is in near contact or contact with the user's forehead thereby limiting movement of the accompanying mask frame and mask cushion towards to the user's face in the region of the nasal bridge. This stabilising feature is achieved due to the relatively rigid engagement of the brace in relation to the mask shell.

FIGS. 5A-5D show schematically, multiple views of a version of a brace according to the present invention suitable for use with a MIRAGE® full-face mask system by the present applicant. The brace is constructed of 2.5 mm gauge mild steel wire butt-welded so as to assume a continuous form. The wire is bent to the appropriate configuration using standard wire bending techniques which may include automated bending by way of a suitably programmed NC wire bending machine.

Preferably the resulting brace is powder coated so as to provide for a corrosive resistant and easily cleaned surface.

Mask shells are typically molded from polycarbonate or similar material. Such a construction technique requires a relatively expensive molding tool. This means that it is expensive for the manufacturer to change the location of the headgear attachment points if they are molded into the mask shell. In contrast it is relatively cheap to configure and manufacture a brace according to the present invention.

The brace is easily hand fitted to the mask frame and clip set in place as previously described. This manoeuvre being easily achieved by hand, in view of the inherent malleability of the brace material. It is clear that an alternative embodiment could be configured so as to adapt the brace to be received by brace receiving features in a mask frame.

It is also intended that the brace could be configured so as to engage brace receiving features that may be provided by a mask cushion clip 21. In this way the brace may be accurately and securely positioned relative to the mask frame while serving to secure the cushion clip and cushion to the mask frame. The brace engaging feature may be located on the brace with a reciprocal feature on the mask shell or alternatively may be a separate component that engages the brace and the mask shell.

The brace receiving features may either extend around the outer circumference of the mask frame surrounding and securing the mask cushion or may pass through apertures provided for in the mask frame.

The method and mask assembly of the present invention provide further advantages such as allowing for the inclusion of other accessories that would be of benefit to the user, such as provision for holding or attaching a gastro-nasal tube or a sensor for measuring physiological parameters of the user, attaching a tube for the provision of a supplemental gas or pharmaceuticals, or attachment of other accessories such as a device for preventing or inducing the passage of air through the mouth such as is described and depicted in U.S. Pat. No. 6,123,082 (Berthon-Jones, assignee ResMed Limited).

Other benefits of the invention include the ability to disassemble the headgear from the mask while the headgear is engaged with the brace without affecting strap length adjustment in order that the mask shell and cushion may be washed. The benefit of this is that the brace and headgear assembly may be re-attached to the mask frame without requiring the re-adjusting of the strap length.

This is because once the brace is located in the predetermined position relative to the mask frame, the head strap position relative to the mask frame will resume the position it was in at the time that the brace was removed from the mask shell.

By making the mask brace of a malleable material, such as is described above in relation to the preferred embodiment, it will be appreciated that a user can make some adjustment to the position of the headgear retaining portion or the mask stabilising feature or both so as to meet particular needs. This opportunity to make such adjustments allows for rapid tailoring of the mask assembly to a user's particular requirements.

While the preferred embodiment includes description of a mask brace having a clip fit to the mask shell, it is envisaged that the brace might be attached to the mask shell by other means such as a hook and loop system like Velcro™ or other suitable means. Preferably the attachment means achieves a consistent support of the brace relative to the mask frame while located but also allowing for a relatively easy disassembly of the two components in order to facilitate the achievement of other benefits that come with the present invention.

The present invention is particularly suitable for accommodating asymmetrical mask configurations as may be required by users such as those with facial palsy. For example, the present invention allows for the individual configuration of asymmetrical head strap attachment points and use of asymmetrical mask cushions with standard mask frames.

The invention claimed is:

1. A patient interface assembly comprising a mask shell providing a first set of headgear connection points, a mask cushion and a mask cushion clip for attaching the cushion to said shell, the assembly further comprising a brace, the brace being shaped so as to be retainingly engageable with and detachable from the mask shell of the patient interface assembly and providing a second set of headgear member connection points for engagement with a headgear member, wherein the brace includes an elongate member shaped so as to be engageable by formations on the mask shell of the patient interface assembly.

2. An assembly according to claim 1, wherein the elongate member is shaped so as to be engageable between opposed formations on the mask shell of the patient interface assembly.

3. An assembly according to claim 2, wherein one of the formations is a peripheral flange of the mask shell of the patient interface assembly.

4. An assembly according to claim 2, wherein at least one of the formations is a headgear member connection point on the mask shell patient interface assembly.

5. An assembly according to claim 1, wherein the elongate member is formed by wire bent to conform to the shape of the mask shell of the patient interface assembly and to provide the second set of headgear member connection points.

6. An assembly according to claim 5, wherein the headgear member connection points are formed by local bending of the wire into a U shape.

7. An assembly according to claim 1, wherein the mask shell is relatively rigid.

8. An assembly according to claim 1, wherein the elongate member further includes a portion adapted to be disposed in the region of the patient's forehead.

9. An assembly according to claim 8, wherein at least one headgear member connection point is located in the portion adapted to be disposed in the region of the patient's forehead.

10. An assembly according to claim 9, wherein the portion adapted to be disposed in the region of the patient's forehead extends beyond the mask shell.

11. An assembly according to claim 10, wherein the portion adapted to be disposed in the region of the patient's forehead is configured to contact the patient's forehead and limit movement of the assembly toward the patient's nasal bridge when the assembly is mounted on the patient's face.

12. An assembly according to claim 1, wherein the brace engages the mask shell and a cushion clip to secure the cushion clip to the shell.

13. An assembly according to claim 1, wherein the first set of headgear member connection points provide a different headgear member alignment from that provided by the second set of headgear member connection points.

14. An assembly according to claim 12, wherein at least one of the headgear member connection points of the mask shell functions as a point of engagement between the brace and the mask shell.

15. An assembly according to claim 1, wherein the elongate member is malleable.

16. An assembly according to claim 1, further comprising headgear, the headgear engaging the first and second sets of headgear member connection points.

17. An assembly according to claim 1, further comprising a brace receiving member configured to receive the brace and secure the brace to the mask shell.

18. An assembly according to claim 17, further comprising a cushion clip that includes the brace receiving member, and wherein the brace engages the mask shell and the cushion clip to secure the cushion clip to the shell.

19. An assembly according to claim 17, wherein the brace receiving member includes a first portion located on the brace and a second portion located on the mask shell, the first and second portion of the brace receiving member being configured to engage each other and secure the brace to the mask shell when the brace is mounted on the mask shell.

20. An assembly according to claim 17, wherein the brace receiving member extends around an outer circumference of the mask shell.

21. An assembly according to claim 17, wherein the brace receiving member passes through apertures in the mask shell.

22. An assembly according to claim 17, wherein the brace receiving member is a hook and loop system.

\* \* \* \* \*